United States Patent [19]

Gastrock et al.

[11] Patent Number: 4,683,324

[45] Date of Patent: Jul. 28, 1987

[54] PROCESS FOR THE RESOLUTION OF CERTAIN RACEMIC AMINO NITRILES

[75] Inventors: William H. Gastrock, Hightstown; Peter J. Wepplo, Princeton, both of N.J.

[73] Assignee: American Cyanamid Company, Stamford, Conn.

[21] Appl. No.: 381,828

[22] Filed: May 25, 1982

[51] Int. Cl.$^4$ ............................................ C07C 121/42
[52] U.S. Cl. .................................................. 558/354
[58] Field of Search ...................... 260/465.5 R, 464; 558/354

[56] References Cited

U.S. PATENT DOCUMENTS

| | | | |
|---|---|---|---|
| 2,841,609 | 2/1958 | Larsen et al. | 260/465 E |
| 3,808,254 | 4/1974 | Matthews | 260/465 E X |
| 4,072,698 | 2/1978 | Hylton et al. | 260/465.5 R X |
| 4,183,865 | 1/1980 | Hohnjec et al. | 260/465.5 R |
| 4,305,887 | 12/1981 | Herrling | 260/465 E |

OTHER PUBLICATIONS

Noller, "Chemistry of Organic Compounds", 3rd ed., (1965), pp. 363–364, Sounders Co., Philadalphia.

*Primary Examiner*—Joseph Paul Brust
*Attorney, Agent, or Firm*—H. G. Jackson

[57] ABSTRACT

The invention is a process for the selective and concomitant resolution-racemization-resolution of certain substituted, racemic amino nitriles via their respective tartrate salts. The invention further relates to certain resolved (optically active) amino amides prepared from said amino nitriles, and to the herbicidal substituted oxo-imidazolinyl nicotinic acids and 3-quinoline carboxylic acids prepared therefrom.

4 Claims, No Drawings

PROCESS FOR THE RESOLUTION OF CERTAIN RACEMIC AMINO NITRILES

SUMMARY OF THE INVENTION

The invention is a process for the selective and concomitant resolution-racemization-resolution of certain racemic amino nitriles via their tartrate salts. The amino nitriles of the present invention may be represented by formula (I):

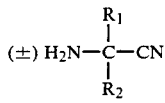

wherein $R_1$ is $C_1$-$C_4$ alkyl; $R_2$ is $C_1$-$C_4$ alkyl or $C_3$-$C_6$ cycloalkyl; with the proviso that when $R_1$ and $R_2$ are selected from $C_1$-$C_4$ alkyl they cannot be the same.

The most preferred formula (I) compound is:

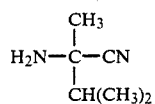

The above formula (I) unresolved or resolved amino nitriles are useful and valuable intermediates by themselves, and especially when first hydrolyzed to the corresponding amides of formula (II):

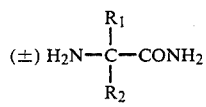

wherein $R_1$ and $R_2$ are as hereinabove defined, for the preparation of herbicidal 2-(5,5-disubstituted-4-oxo-2-imidazolin-2-yl) nicotinic acids and 3-quinolinecarbo acids of formula (III):

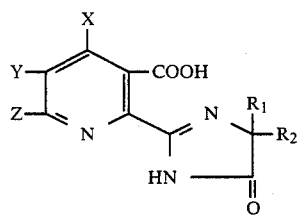

wherein $R_1$ and $R_2$ are as defined above; X is hydrogen or $C_1$-$C_4$ alkyl; Y is selected from the group consisting of hydrogen, halogen, $C_1$-$C_4$ alkyl, $C_1$-$C_4$ alkoxy, trifluoromethyl, trichloromethyl, difluoromethyl, di ($C_1$-$C_4$) alkylamino, $C_1$-$C_4$ alkylthio, phenyl, phenoxy or phenyl or phenoxy substituted with one $C_1$-$C_4$ alkyl, $C_1$-$C_4$ alkoxy or halogen; Z is selected from the group consisting of hydrogen, $C_1$-$C_4$ alkyl, trifluoromethyl, trichloromethyl, phenyl or phenyl substituted with one $C_1$-$C_4$ alkyl or alkenyl, $C_1$-$C_4$ alkoxy or halogen; and, When taken together Y and Z may form a ring in which YZ is represented by the structure: —$(CH_2)_n$—wherein n is an integer selected from 3 to 5 provided that X is hydrogen; or YZ is

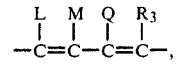

Where L, M, Q and $R_3$ each represent members selected from the group consisting of hydrogen, halogen, $C_1$-$C_4$ alkyl, $C_1$-$C_4$ alkoxy, $C_1$-$C_4$ haloalkyl, difluoromethoxy, diloweralkylamino, $C_1$-$C_4$ alkylthio, nitro, phenyl, phenoxy, or mono-substituted phenyl or phenoxy where the substituent is one $C_1$-$C_4$ alkyl, $C_1$-$C_4$ alkoxy or halogen, with the proviso that only one of the L, M, Q or $R_3$, may represent a substituent other than hydrogen, halogen, $C_1$-$C_4$ alkyl or $C_1$-$C_4$ alkoxy; the racemates, the optical isomers thereof, and the salts thereof.

The racemic mixtures of the formula (I) amino nitriles may be resolved into their optical isomers by customary means, as by selectively precipitating one or the other isomer with the appropriate (+) or (−) optical isomer of an acid, such as tartaric acid. Next, the. (+) or (−)-amino nitrile is regenerated from its salt with a base such as ammonium hydroxide, isolated and re-precipitated again with the appropriate (+) or (−)-acid. Usually, this cycle will have to be repeated several times until the desired optical isomer is obtained in satisfactory optical purity. Unfortunately, however, in the course of such manipulations, considerable material losses occur.

We now find, that by the process of the present invention the desired optical isomer is obtained in high optical purity after one precipitation from the racemic mixture We also find, that under the conditions and in the course of this novel process, the equilibrium of the optieal isomers present in the racemic mixture is shifted in favor of the desired isomer. That is, while the desired isomer is being precipitated as its salt by the appropriate resolved acid from the racemic mixture, the unwanted isomer concomitantly racemizes under the conditions of the process, thereby yielding additional quantities of said desired isomer. The thus-formed desired isomer is rapidly precipitated from the mixture in the form of its salt by the optically active acid leaving behind the unwanted isomer. This isomer will again racemize, providing more of the desired isomer and this process repeats itself continuously until it reaches its practical limits or is terminated. This way, and depending on the conditions of the resolution process of the invention, up to a theoretical quantity (by weight) of the original racemic mixture may be recovered in the form of one or the other optical isomer, as desired.

Conveniently, by the concomitant resolution-racemization-resolution process of the invention, resolved (+) or (−)-tartaric acid is dissolved in a solvent selected from methanol, ethanol, 2-propanol preferably anhydrous methanol, or in a mixture of methanol/methylene chloride, in amounts of from about 0.5 mole to about 1.2 mole and preferably from about 0.75 to about 1.0 mole per mole of unresolved amino nitrile. Next, the appropriate unresolved amino nitrile of formula (I) is added in small portions to the above solution of tartaric acid, neat, or if desired as a solution prepared with the solvent selected for said process. The mixture is maintained at a temperature range of from about 5° C. to about 50° C.,and preferably from about 15° C. to about 40° C.,for a period of time from about one to about 40 hours and preferably from about 4 to about 24 hours.

We also find that in the course of the above resolution-racemization process the amino nitriles of formula (I) have a tendency to decompose with the concomitant evolution of HCN and that this may be suppressed by the addition of from about 0.1 mole to about 1.0 mole and preferably from about 0.4 to about 0.6 mole of HCN per mole of amino nitrile. Addition of HCN to the above resolution-racemization process affords higher yields than would be otherwise obtainable.

As stated above, formula (I) amino nitriles are useful and valuable intermediates per se, but especially when hydrolyzed to the corresponding amides of formula (II) for the preparation of herbicidal substituted oxo-imidazolinyl nicotinic and quinoline carboxylic acids of formula (III).

There are a number of routes disclosed and discussed in Application for United States Letters Patent of Marinus Los, Ser. No. 382,041, filed concurrently herewith and now U.S. Pat. No 4,638,068 and incorporated herein by reference thereto pertaining to the preparation of said formula (III) herbicides from the appropriate amino nitriles of formula (I) or the amino amides of formula (II). The following route is shown to illustrate one such preparation of said herbicides:

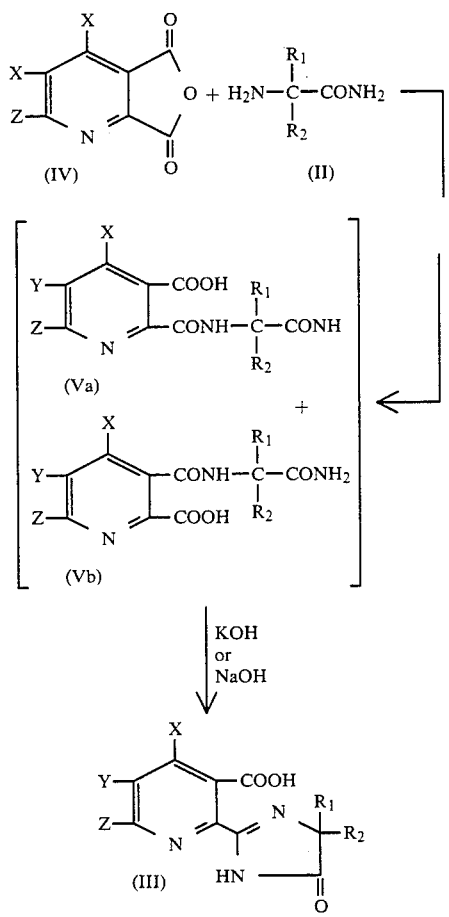

wherein X, Y, Z, $R_1$ and $R_2$ are as hereinabove defined.

Thus, a quinolinic acid anhydride of formula (IV) is reacted with the appropriately substituted amide of formula (II) to yield a mixture of the monoamides of quinolinic acid of formula (Va) and (Vb), followed by the base-catalyzed cyclization of the amide of formula (Va) to afford the herbicides of formula (III).

The above described and illustrated basecatalyzed cyclization of formula (IVa) and (IVb) amides is described in the application for U.S. Letters Patent of Jerry Michael Barton, Don Wesley Long and Kenneth Dale Lotts, Ser. No. 381,818, filed concurrently herewith and incorporated herein by reference thereto and is now U.S. Pat. No. 4,578,780 (1985).

Obviously by using the resolved optically active amides of formula (II) in the above reaction sequence, the appropriate optically active herbicides of formula (III) are obtained.

It should be noted here that hydrolysis of (+) amino nitriles of formula (I) affords the (−) amino amides of formula (II) and hydrolysis of (−) amino nitriles of formula (I) affords the (+) amino amides of formula (II), respectively. The hydrolysis of the above nitriles to their respective amides may be achieved by a variety of conventional procedures, conveniently, with concentrated sulfuric acid.

The formula (III) 2-(5,5-disubstituted-4-oxo-2-imidazolin-2-yl)nicotinic acids and 3-quinolinecarboxylic acids are highly effective herbicidal agents useful for the control of a wide variety of monocotyledonous and dicotyledonous plants, applied to the foliage thereof, or to the soil containing seeds or other propagating organs of said plants such as tubers, rhizomes or stolons, at rates of from about 0.025 to 8.0 kg/ha, and preferably at rates from about 0.032 to 4.0 kg/ha.

The formula (III) herbicides can be formulated as wettable powders, flowable concentrates, emulsifiable concentrates, granular formulations, and the like.

Wettable powders can be prepared by grinding together about 20% to 45% by weight of a finely divided carrier such as kaolin, bentonite, diatomaceous earth, attapulgite, or the like, 45% to 80% by weight of the active compound, 2% to 5% by weight of a dispersing agent such as sodium lignosulfonate, and 2% to 5% by weight of a nonionic surfactant, such as octylphenoxy polyethoxy ethanol, nonylphenoxy polyethoxy ethanol, or the like.

A typical flowable liquid can be prepared by admixing about 40% by weight of the active ingredient with about 2% by weight of a gelling agent such as bentonite, 3% by weight of a dispersing agent such as sodium lignosulfonate, 1% by weight of polyethylene glycol and 54% by weight of water.

A typical emulsifiable concentrate can be prepared by dissolving about 5% to 25% by weight of the active ingredient in about 65% to 90% by weight of N-methylpyrrolidone, isophorone, butyl cellosolve, methylacetate, or the like and dispersing therein about 5% to 10% by weight of a nonionic surfactant such as alkylphenoxy polyethoxy alcohol. This concentrate is dispersed in water for application as a liquid spray.

Where soil treatments are involved, the compounds may be prepared and applied as granular products. Preparation of the granular product can be achieved by dissolving the active compound in a solvent such as methylene chloride, N-methylpyrrolidone, or the like and spraying the thus-prepared solution on a granular carrier such as corncob grits, sand, attapulgite, kaolin, or the like.

The granular product thus prepared generally comprises about 3% to 20% by weight of the active ingredient and about 97% to 80% by weight of the granular carrier.

In order to facilitate a further understanding of the invention, the following examples are presented primarily for the purpose of illustrating certain more specific details thereof. The invention is not to be deemed limited thereby except as defined in the claims.

EXAMPLE 1

Resolution-racemization of 2-amino-2,3-dimethylbutyronitrile

A solution of 33.8 g (0.225 mol) of D-(−)-tartaric acid in 120 ml of anhydrous methanol is stirred and 28.0 g (0.25 mol) of (±)-2-amino-2,3-dimethylbutyronitrile is added dropwise. The resulting mixture is stirred at ambient temperature for 22 hours, the solid is then filtered and washed with 15 ml of methanol. Drying affords 55.4 g of (−)-2-amino-2,3-dimethylbutyronitrile-(−)-hemitartrate. A slurry of 10.4 g of the above salt in 40 ml of water is basified with 6.8 ml of concentrated ammonia. The solution is extracted with methylene chloride. The organic phase is dried over sodium sulfate and evaporated to afford 3.98 g of (−)-2-amino-2,3-dimethylbutyronitrile $[\alpha]_D = -6.36°$ (c =0.0355 g/ml THF).

Following the above process, addition of 2.7 g HCN prior to the addition of the (±)-2-amino-2,3-dimethylbutyronitrile results in the isolation of 55.58 g of hemitartrate salt. Treatment of 10.4 g of salt with aqueous sodium hydroxide followed by extraction with methylene chloride affords 4.13 g of title compound $[\alpha]_D = -6.40°$ (c=0.03346 g/ml THF).

By the above procedure, several preparations are compiled in Table I attached hereto.

nitrogen atmosphere at 15° to 18° C. and 28.0 g (0.25 mol) of (±)-2-amino-2,3-dimethylbutyronitrile is added dropwise over 40 minutes and the mixture is then stirred at ambient temperature for 16 hours. The mixture is cooled to 4° C.,the solid is filtered and washed with 5 ml of methanol. Drying affords 61.2 g of (+)-2-amino-2,3-dimethylbutyronitrile-(+) hemitartrate. A slurry of 10.4 g of the salt and 30 ml of water is cooled in an ice bath and basified with 6.8 ml of concentrated ammonia. The solution is extracted with methylene chloride, the organic phase is dried over sodium sulfate and evaporated to afford 3.75 g of (+)-2-amino-2,3-dimethylbutyronitrile, $[\alpha]_D = +6.57°$ (c =0.0332 g/ml THF).

Following the above process, addition of 2.7 g (0.10 mol) of HCN prior to the addition of the (±) 2-amino-2,3-dimethylbutyronitrile to the reaction mixture results in 56.7 g of the hemitartrate salt. By a neutralization and extraction procedure similar to that described above, 10.4 g salt affords 4.22 g title product, $[\alpha]_D = +6.32°$ (c=0.03306 g/ml THF).

In a similar manner, replacing the methanol with anhydrous ethanol in the above process, results in the isolation of 56.16 g of dry hemitartrate salt. By a neutralization and extraction procedure similar to that described above, 10.4 g of salt affords 4.1 g of (+)-2-amino-2,3-dimethylbutyronitrile $[\alpha]_D = +3.10°$ (c=0.03385 g/ml THF).

By the above procedure, several preparations are made. The pertinent data of these preparations are compiled in Table II attached hereto.

TABLE I

Resolution of racemic 2-amino-2,3-dimethylaminobutyronitrile by the process of the invention via the tartrate salt

| Exp No | Molar ratio[1] of acid to nitrile | Solvent | temp in °C. | time in h | wt % of nitrile obtained from racemate | Optical yield[2] % | $[\alpha]_D$ | % optical[3] purity |
|---|---|---|---|---|---|---|---|---|
| 1 | 0.8 | CH₃OH | 12-20 | 16 | 64.6 | 54.7 | −6.19 | 84.7 |
| 2 | 0.9 | CH₃OH | 10-17 | 16 | 71.6 | 56.8 | −5.65 | 79.3 |
| 3 | 0.9 | CH₃OH | 20-23 | 40 | 69.2 | 60.2 | −6.36 | 87.0 |
| 4 | 1.0 | CH₃OH | 37-40 | 6.5 | | | | |
|   |     | *     | 23    | 16  | 81.2 | 66.3 | −5.97 | 81.7 |
| 5 | 0.9 | CH₃OH | 19-22 | 20 | 75.7 | 65.9 | −6.36 | 87.0 |
| 6 | 1.0 | CH₃OH | 22 | 43 | 74.0 | 67.8 | −6.70 | 91.6 |
| 7 | 0.9 | CH₃OH | 20-22 | 20.5 | 71.6 | 60.4 | −6.17 | 84.4 |
| 8 | 0.9 | CH₃OH + HCN | 13-23 | 20 | 78.7 | 68.9 | −6.40 | 87.5 |

[1] the molar ratio of (−) tartaric acid to racemic aminonitrile
[2] wt % of resolved nitrile isolated multiplied by the optical purity divided by 100; e.g. $\frac{64.6 \times 84.7}{100} = 54.7$ (example 1)
[3] observed specific rotation, $[\alpha]_D$, divided by maximum specific rotation (−7.31°) multiplied by 100; e.g. $\frac{-6.19}{-7.31} \times 100 = 84.7\%$ (example 1)
* = reaction was run concurrently at two temperature ranges

EXAMPLE 2

Resolution-racemization of 2-amino-2,3-dimethylbutyronitrile

A mixture of 120 ml of anhydrous methanol and 33.8 g (0.225 mol) of L-(+)-tartaric acid is stirred under a

TABLE II

Resolution of racemic 2-amino-2,3-dimethylbutyronitrile by the process of the invention via the tartrate salt

| Exp No | Molar ratio[1] of acid to nitrile | Solvent | temp in °C. | time in h | wt % of nitrile obtained from racemate | Optical yield[2] % | $[\alpha]_D$ | % optical[3] purity |
|---|---|---|---|---|---|---|---|---|
| 1 | 0.9 | CH₃OH | 15-20 | 16 | 78.8 | 70.8 | +6.57 | 89.8 |
| 2 | 0.9 | CH₃OH + CH₂Cl | 20-22 | 17 | 77.9 | 68.7 | +6.44 | 88.2 |
| 3 | 0.85 | CH₃OH | 50 | 1.5 | 64.4 | 57.8 | +6.56 | 89.8 |
| 4 | 0.9 | CH₃OH | 17-22 | 23 | 82.0 | 70.9 | +6.32 | 86.5 |

TABLE II-continued

Resolution of racemic 2-amino-2,3-dimethylbutyronitrile by the process of the invention via the tartrate salt

| Exp No | Molar ratio[1] of acid to nitrile | Solvent | temp in °C. | time in h | wt % of nitrile obtained from racemate | Optical yield[2] % | $[\alpha]_D$ | % optical[3] purity |
|---|---|---|---|---|---|---|---|---|
| 5 | 0.9 | + HCN $C_2H_5OH$ | 17–23 | 23 | 78.9 | 33.5 | +3.10 | 42.4 |

[1] the molar ratio of (+) tartaric acid to racemic aminonitrile

[2] wt % of resolved nitrile isolated multiplied by the optical purity divided by 100; e.g. $\frac{64.6 \times 84.7}{100} = 54.7$ (example 1)

[3] observed specific rotation, $[\alpha]_D$, divided by maximum specific rotation (−7.31°) multiplied by 100; e.g. $\frac{-6.19}{-7.31} \times 100 = 84.7\%$ (example 1)

EXAMPLE 3

Resolution of racemic 2-amino-2,3-dimethylbutyronitrile

To an ice-cold solution of 80 g (+)-tartaric acid in 200 ml water is added 56 g of -2-amino-2,3-dimethylbutyronitrile. During the addition, the mixture is kept cold. The precipitate is collected by filtration, washed with a small amount of ice-cold water and air dried to yield 65.25 g tartrate salt "B".

The filtrate from "B" is treated with 56 ml of concentrated ammonia and extracted 3 times with ether, the combined extracts are washed with brine, dried and concentrated to yield 24.0 g of (−)-2-amino-2,3-dimethylbutyronitrile "A", $[\alpha]_D^{25} = -4.49°$ (c=0.0376 g/ml THF).

The )-amino nitrile ("A") is converted to the tartrate salt with a solution of 39.0 g of (−)-tartaric acid in 54 ml of water, the precipitated salt is collected and the (−)-amino nitrile recovered from the salt with 26 ml of concentrated ammonium hydroxide as described above to afford 19.3 g of (−)-2-amino-2,3-dimethylbutyronitrile with $[\alpha]_D^{25} = 5.89°$ (c =0.0353 g/ml THF).

Two additional cycles of salt preparation and liberation of the (−)-amino nitrile afford 11.8 g of assumed to be optically pure (−)-2-amino-2,3-dimethylbutyronitrile ("A") with $[\alpha]_D^{25} = -7.31°$ (c=0.0368 g/ml THF).

When the above obtained (+)-tartrate salt ("B") of (+)-2-amino-2,3-dimethylbutyronitrile is put through the same sequence of liberation of amino nitrile and salt formation with (+)-tartaric acid two times, the (+)-2-amino-2,3dimethylbutyronitrile obtained has $[\alpha]_D^{25} = +6.93°$ (c=0.085 g/ml THF).

EXAMPLE 4

Preparation of (+)-2-amino-2,3-dimethylbutyramide

A solution of 3.0 g of (−)-2-amino-2,3-dimethylbutyronitrile, $[\alpha]_D = -6.71°$ (c=0.03307 g/ml THF) in 10 ml methylene chloride is added with stirring at 80° C. to 13.95 g of concentrated sulfuric acid. The solution is heated for one hour, allowed to cool and 14 g of ice is added. Next, 27 ml of concentrated ammonia is added while cooling. The resulting solution is extracted with methylene chloride (5×25 ml). The combined extracts are dried and evaporated to dryness to afford 3.23 g of title product, mp 81°–83° C., $[\alpha]_D = +53.04°$ (c =0.0313 g/ml THF).

EXAMPLE 5

Preparation of (+), (−) and (+)-2-amino-2,3-dimethylbutyramide

Concentrated sulfuric acid (20.7 ml) is cooled with stirring in an ice-acetone bath. To the acid is added 11.8 g of (−)-2-amino-2,3-dimethylbutyronitrile $[\alpha]_D^{25} = -7.31°$ (c=0.0368 g/ml THF) at such a rate that the temperature does not exceed 25° C. After the addition is completed, the temperature of the reaction mixture is raised slowly to 100° C. and held at that temperature for one hour. After cooling the mixture in an ice-acetone bath, 85 ml of concentrated ammonia is added at such a rate that the temperature does not exceed 25° C. The mixture is extracted five times with methylene chloride, the combined extracts dried and concentrated to afford 11.95 g of a white solid, mp 79°–81° C. and $[\alpha]_D^{25} = +57.43°$ (c=0.0213 g/ml THF). This solid is recrystallized from methylene chloridehexane to give 11.2 g of (+)-2-amino-2,3-dimethylbutyramide, mp 81°–82° C., $[\alpha]_D^{25} +59.38°$ (c=0.0162 g/ml THF) and assumed to be optically pure.

Similarly, hydrolysis of (+)-2-amino-2,3.-dimethylbutyronitrile with sulfuric acid yields (−)-2-amino-2,3-dimethylbutyramide, mp 81°–82° C., $[\alpha]_D^{25} = -57.14°$ (c =0.0654 g/ml THF); and hydrolysis of (±)2-amino-2,3-dimethylbutyronitrile with sulfuric acid yields (±)-2-amino2,3dimethylbutyramide, mp 74.5°–76° C.

EXAMPLE 6

Preparation of Racemic 2-(5-isopropyl-5-methyl-4-oxo-2-imidazolin-2-yl)nicotinic acid and the Optical Isomers Thereof To a stirred suspension of 2,3-pyridinedicarboxylic anhydride (30 g) in 150 ml of acetonitrile is added a solution of racemic 2-amino-2,3-dimethylbutyramide (28 g) in 140 ml of acetonitrile at 25° to 30° C. The mixture is stirred for 2 hours. The solvent is removed at 50° C. and reduced pressure. The residual gum is dissolved in 230 ml of 2.6 N sodium hydroxide and heated to 80° C. for 1.5 hours.

The mixture is cooled to 25° C. and acidified to a pH of 3 with 65 ml of 37% hydrochloric acid. The resulting solution is extracted with two 200-ml portions of methylene chloride. The extracts are concentrated to a residue of 33 g of the desired product, mp 160°–165° C.

After standing overnight, the aqueous layer deposits 3.8 g of the picolinic acid isomer, mp 155°–157° C. (dec.).

Substituting (+) and (−)-2-amino-2,3-dimethylbutyramide in the above reaction affords (+)-2-(5isopropyl-5-methyl-4-oxo-2-imidazolin-2-yl)nicotinic acid, mp 128°-131° C., $[\alpha]_D^{25} = +18.37°$ (c=0.0902 g/ml THF), and (−)-2-isopropyl-5-methyl-4oxo-2-imidazolin-2-yl)nicotinic acid, mp 132°-134° C., $[\alpha]_D^{25} = -18.14°$ (C=0.0896 g/ml THF) respectively.

EXAMPLE 7

Preparation of racemic 2-(5-isopropyl-5-methyl-4-oxo-2-imidazolin-2-yl)-3-quinolinecarboxylic acid and the optical isomers thereof To a stirred solution of 2-amino-2,3-dimethylbutyramide (40 g) in 500 ml of acetonitrile is added 60 g of 2,3-quinolinedicarboxylic anhydride in portions during about 45 minutes. The mixture is heated to 50°-60° C. for two hours, cooled to room temperature and filtered to give 73.7 g of the mixture of carbamoylquinolinecarboxylic acids.

This solid is dissolved in 435 ml of 1.5 N sodium hydroxide and heated for two hours at 80°-85° C. The solution is cooled and acidified with 57 ml of 37% hydrochloric acid. The desired product is removed by filtration and dried. The solid is recrystallized from methanol to give 49 g of racemic 2-(5-isopropyl-5-methyl-4-oxo-2-imidazolin-2-yl)-3-quinolinecarboxylic acid, mp 240°-242° C.

Substituting (+) and (−)-2-amino-2,3-dimethylbutyramide in the above reaction affords (+)-2-(5-isopropyl-5-methyl-4-oxo-2-imidazolin-2-yl)-3-quinolinecarboxylic acid, mp 228°-236.5° C., $[\alpha]_D^{25} = +28.5°$ (c=0.0105 g/ml CH$_2$Cl$_2$) and (−) -2-isopropyl-5-methyl-4-oxo-2-imidazolin-2-yl)-3-quinolinecarboxylic acid, mp 227°-237° C., $[\alpha]_D^{25} = -29.2°$ (C=0.0095 g/ml CH$_2$Cl$_2$) respectively.

EXAMPLE 8

Post-emergence Herbicidal Evaluation of Test Compounds

The postemergence herbicidal activity of the compounds is demonstrated by the following tests, wherein a variety of monocotyledonous and dicotyledonous plants are treated with test compounds dispersed in aqueous acetone mixtures. In the tests, seedling plants are grown in jiffy flats for about two weeks. The test compounds are dispersed in 50/50 acetone/water mixtures containing 0.5% TWEEN ® 20, a polyoxyethylene sorbitan monolaurate surfactant of Atlas Chemical Industries, in sufficient quantity to provide the the equivalent of about 0.016 to 10 kg per hectare of active compound when applied to the plants through a spray nozzle operating at 2.8 kg cm$^{-2}$ pressure for a predetermined time. After spraying plants are placed on greenhouse benches and are cared for in the usual manner, commensurate with conventional greenhouse practices. From 4 to 5 weeks after treatment, the seedling plants, are examined and rated according to the rating system provided below. The data obtained are recorded in Table III below.

| Rating System | % Difference in Growth from the Check* |
|---|---|
| 0 — No effect | 0 |
| 1 — Possible effect | 1–10 |
| 2 — Slight effect | 11–25 |
| 3 — Moderate effect | 26–40 |
| 5 — Definite injury | 41–60 |
| 6 — Herbicidal effect | 61–75 |
| 7 — Good herbicidal effect | 76–90 |
| 8 — Approaching complete kill | 91–99 |
| 9 — Complete kill | 100 |
| 4 — Abnormal growth, that is, a definite physiological malformation but with an over-all effect less than a 5 on the rating scale. | |

In many cases the data are for a single test, but in several instances, they are average values obtained from more than one test.

| Plant Species Used | |
|---|---|
| Barnyardgrass | (*Echinochloa crusgalli*) |
| Green foxtail | (*Setaria viridis*) |
| Purple Nutsedge | (*Cyperus rotundus* L.) |
| Wild Oats | (*Avena fatua*) |
| Quackgrass | (*Agropyron repens*) |
| Field Bindweed | (*Convolvulus arvensis* L.) |
| Morningglory | (*Ipomoea purpurea*) |
| Ragweed | (*Ambrosia artemisiifolia*) |
| Velvetleaf | (*Abutilon theophrasti*) |
| Barley | (*Hordeum vulgare*) |
| Corn | (*Zea mays*) |
| Cotton | (*Gossypium hirsutum*) |
| Rice | (*Oryza sativa*) |
| Soybean | (*Glycine max*) |

TABLE III

Postemergence herbicidal evaluation of test compounds
POST-EMERGENCE TESTS - RATES IN KG/HA

| Compound | RATE | BARN-YARD-GRASS | GREEN FOX-TAIL | PURPLE NUT-SEDGE | WILD OATS | QUACK GRASS | FIELD BIND-WEED | MORNING-GLORY SP | RAG-WEED |
|---|---|---|---|---|---|---|---|---|---|
| (+)-2-(5-iso-propyl-5-methyl-4-oxo-2-imida-zolin-2-yl)-nicotinic acid | 1.000 | 9.0 | 9.0 | 9.0 | 9.0 | 9.0 | 9.0 | 9.0 | 9.0 |
| | .500 | 9.0 | 9.0 | 9.0 | 9.0 | 9.0 | 9.0 | 9.0 | 9.0 |
| | .250 | 9.0 | 9.0 | 9.0 | 9.0 | 9.0 | 9.0 | 9.0 | 9.0 |
| | .125 | 9.0 | 9.0 | 9.0 | 9.0 | 9.0 | 9.0 | 9.0 | 9.0 |
| (−)-2-(5-Iso-propyl-5-methyl-4-oxo-2-imida-zolin-2-yl)-nicotinic acid | 1.000 | 9.0 | 9.0 | 9.0 | 9.0 | 9.0 | 9.0 | 9.0 | 9.0 |
| | .500 | 9.0 | 9.0 | 8.0 | 9.0 | 9.0 | 9.0 | 9.0 | 9.0 |
| | .250 | 9.0 | 9.0 | 8.0 | 9.0 | 9.0 | 9.0 | 9.0 | 3.0 |
| | .125 | 9.0 | 9.0 | 6.0 | 9.0 | 8.0 | 9.0 | 9.0 | 7.0 |
| | .063 | 6.0 | 9.0 | 5.0 | 9.0 | 9.0 | 9.0 | 9.0 | 4.0 |
| | .032 | 6.0 | 9.0 | 2.0 | 8.0 | 8.0 | 9.0 | 4.0 | 1.0 |
| 2-(5-Isopropyl-5-methyl-4-oxo-2-imidazolin-2-yl)nicotinic acid | 10.000 | 9.0 | 9.0 | 9.0 | 9.0 | | | 7.0 | 9.0 |
| | 2.000 | 9.0 | 9.0 | 9.0 | 9.0 | | | 8.0 | 8.0 |
| | 1.000 | 9.0 | 9.0 | 9.0 | 9.0 | 9.0 | 8.8 | 8.8 | 8.8 |
| | .500 | 9.0 | 9.0 | 8.7 | 9.0 | 9.0 | 9.0 | 8.8 | 8.6 |
| | .250 | 8.9 | 9.0 | 8.8 | 9.0 | 9.0 | 9.0 | 8.9 | 8.6 |
| | .125 | 9.0 | 9.0 | 8.4 | 9.0 | 8.9 | 8.9 | 8.9 | 7.4 |
| (−)-2-(5-Iso-propyl-5-methyl- | 1.000 | 8.8 | 9.0 | 7.0 | | 8.8 | 8.3 | 6.8 | 8.0 |
| | .800 | 8.8 | 9.0 | 5.8 | | 8.3 | 8.8 | 6.3 | 8.0 |

TABLE III-continued

Postemergence herbicidal evaluation of test compounds
POST-EMERGENCE TESTS - RATES IN KG/HA

| Compound | | | | | | | | |
|---|---|---|---|---|---|---|---|---|
| 4-oxo-2-imida- | .500 | 8.5 | 8.8 | 5.8 | | 7.5 | 8.0 | 5.5 | 7.8 |
| zolin-2-yl)-3- | .400 | 8.5 | 8.5 | 5.5 | | 7.3 | 7.8 | 5.3 | 7.8 |
| quinolinecarbo- | .300 | 7.8 | 8.5 | 4.5 | | 7.3 | 7.5 | 4.8 | 7.5 |
| xylic acid | | | | | | | | | |
| (+)-2-(5-iso- | 1.000 | 9.0 | 9.0 | 7.0 | | 8.8 | 8.8 | 8.0 | 9.0 |
| propyl-5-methyl- | .800 | 9.0 | 9.0 | 7.3 | | 9.0 | 9.0 | 7.8 | 9.0 |
| zolin-2-yl)-3- | .500 | 9.0 | 9.0 | 6.8 | | 8.8 | 9.0 | 7.0 | 8.8 |
| quinolinecarbo- | .400 | 8.8 | 9.0 | 6.8 | | 8.3 | 9.0 | 7.0 | 7.8 |
| xylic acid | .300 | 8.8 | 8.8 | 6.8 | | 7.8 | 8.7 | 6.3 | 8.0 |
| 2-(5-Isopropyl- | 8.000 | 9.0 | 9.0 | 9.0 | 9.0 | 9.0 | 9.0 | 9.0 | |
| 5-methyl-4-oxo- | 4.000 | 9.0 | 9.0 | 9.0 | 9.0 | 9.0 | 9.0 | 8.5 | 9.0 |
| 2-imidazolin-2- | 2.000 | 9.0 | 9.0 | 8.5 | 9.0 | 9.0 | 9.0 | 8.3 | 8.5 |
| yl)-3-quinoline- | 1.000 | 9.0 | 9.0 | 8.3 | 9.0 | 8.9 | 8.7 | 8.3 | 8.8 |
| carboxylic acid | .800 | 9.0 | 8.8 | 6.8 | | 8.8 | 8.8 | 6.8 | 8.0 |
| racemic mixture | .500 | 8.9 | 8.9 | 7.6 | 9.0 | 8.6 | 8.3 | 7.7 | 8.4 |

| Compound | RATE | VELVET-LEAF | S BARLEY LA | CORN FIELD | RICE, NATO | SOY-BEAN WI | SUN-FLOWER XXX | SOY-BEAN AD |
|---|---|---|---|---|---|---|---|---|
| (+)-2-(5-iso- | 1.000 | 9.0 | 9.0 | 9.0 | 9.0 | | 9.0 | |
| propyl-5-methyl- | .500 | 9.0 | 9.0 | 9.0 | 9.0 | | 9.0 | |
| 4-oxo-2-imida- | .250 | 9.0 | 9.0 | 9.0 | 9.0 | | 9.0 | |
| zolin-2-yl)- | .125 | 9.0 | 9.0 | 9.0 | 9.0 | | 9.0 | |
| nicotinic acid | | | | | | | | |
| (−)-2-(5-Iso- | 1.000 | 9.0 | 9.0 | 9.0 | 9.0 | 9.0 | 9.0 | |
| propyl-5-methyl- | .500 | 9.0 | 9.0 | 9.0 | 9.0 | 9.0 | 9.0 | |
| 4-oxo-2-imida- | .250 | 9.0 | 9.0 | 9.0 | 9.0 | 9.0 | 9.0 | |
| zolin-2-yl)- | .125 | 9.0 | 9.0 | 9.0 | 9.0 | 9.0 | 7.0 | |
| nicotinic acid | .063 | 9.0 | 9.0 | 9.0 | 9.0 | 9.0 | 6.0 | |
| | .032 | 9.0 | 8.0 | 9.0 | 9.0 | 9.0 | 5.0 | |
| 2-(5-Isopropyl- | 10.000 | 9.0 | | | | | | |
| 5-methyl-4-oxo- | 2.000 | 9.0 | | 9.0 | 9.0 | 9.0 | | |
| 2-imidazolin-2- | 1.000 | 9.0 | 9.0 | 9.0 | 9.0 | 9.0 | 9.0 | |
| yl)nicotinic | .500 | 8.9 | 9.0 | 9.0 | 8.8 | 9.0 | 9.0 | |
| acid | .250 | 8.9 | 9.0 | 9.0 | 8.8 | 9.0 | 9.0 | |
| | .125 | 8.9 | 9.0 | 9.0 | 8.7 | 8.7 | 9.0 | |
| (−)-2-(5-Iso- | 1.000 | 8.8 | | | | | | |
| propyl-5-methyl- | .800 | 8.8 | | | | | | |
| 4-oxo-2-imida- | .500 | 7.5 | | | | | | |
| zolin-2-yl)-3- | .400 | 7.8 | | | | | | |
| quinolinecarbo- | .300 | 7.8 | | | | | | |
| xylic acid | | | | | | | | |
| (+)-2-(5-iso- | 1.000 | 8.8 | | | | | | |
| propyl-5-methyl- | .800 | 9.0 | | | | | | |
| zolin-2-yl)-3- | .500 | 8.8 | | | | | | |
| quinolinecarbo- | .400 | 8.0 | | | | | | |
| xylic acid | .300 | 7.3 | | | | | | |
| 2-(5-Isopropyl- | 8.000 | 9.0 | | | | | | |
| 5-methyl-4-oxo- | 4.000 | 9.0 | | | 9.0 | | | 9.0 |
| 2-imidazolin-2- | 2.000 | 9.0 | | | 9.0 | | | 9.0 |
| yl)-3-quinoline- | 1.000 | 8.6 | | | 9.0 | | | 8.7 |
| carboxylic acid | .800 | 8.3 | | | | | | |
| racemic mixture | .500 | 7.7 | | 9.0 | 9.0 | | | 8.3 |

EXAMPLE 9

Preemergence Herbicidal Evaluation of Test Compounds

The preemergence herbicidal activity of the compounds is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.016 to 10 kg per hectare of test compound per cup. The treated cups are then placed on greenhouse benches, watered and cared for in accordance with conventional greenhouse procedures. From 4 to 5 weeks after treatment, the tests are terminated and each cup is examined and rated according to the rating system set forth above. The herbicidal proficiency of the active ingredients of the present invention is evident from the test results which are recorded in Table IV below. Where more than one test is involved for a given compound, the data are averaged.

TABLE IV

Preemergence herbicidal evaluation of test compounds
PRE-EMERGENCE TESTS - RATES IN KG/HA

| Compound | RATE | BARN-YARD-GRASS | GREEN FOX | PURPLE NUT-SEDGE | WILD OATS | QUACK GRASS | FIELD BIND-WEED | MORNING-GLORY SP |
|---|---|---|---|---|---|---|---|---|
| (+)-2-(5-Isopropyl- | .500 | 9.0 | | 9.0 | 9.0 | 9.0 | 9.0 | 9.0 |
| 5-methyl-4-oxo-2- | .250 | 9.0 | | 9.0 | 9.0 | 9.0 | 9.0 | 9.0 |

TABLE IV-continued

Preemergence herbicidal evaluation of test compounds
PRE-EMERGENCE TESTS - RATES IN KG/HA

| | | | | | | | | |
|---|---|---|---|---|---|---|---|---|
| imidazolin-2-yl)- | .125 | 9.0 | | 9.0 | 9.0 | 9.0 | 9.0 | 9.0 |
| nicotinic acid | .063 | 9.0 | | 9.0 | 9.0 | 9.0 | 9.0 | 9.0 |
| | .032 | 8.0 | | 9.0 | 9.0 | 9.0 | 9.0 | 9.0 |
| | .016 | 8.0 | | 9.0 | 9.0 | 9.0 | 9.0 | 9.0 |
| (−)-2-(5-Iso- | .500 | 9.0 | | 9.0 | 9.0 | 9.0 | 9.0 | 9.0 |
| propyl-5-methyl- | .250 | 9.0 | | 9.0 | 9.0 | 9.0 | 9.0 | 9.0 |
| 4-oxo-2-imida- | .125 | 7.0 | | 9.0 | 9.0 | 9.0 | 9.0 | 9.0 |
| zolin-2-yl)- | .063 | 1.0 | | 8.0 | 3.0 | 9.0 | 9.0 | 9.0 |
| nicotinic acid | .032 | 0.0 | | 5.0 | 1.0 | 9.0 | 9.0 | 8.0 |
| 2-(5-Isopropyl- | 10.000 | 8.0 | 9.0 | 9.0 | 8.0 | | | 8.0 |
| 5-methyl-4-oxo- | 2.000 | 9.0 | 9.0 | 9.0 | 9.0 | | | 8.0 |
| 2-imidazolin-2- | 1.000 | 9.0 | 9.0 | 9.0 | 9.0 | 9.0 | 9.0 | 8.0 |
| yl)nicotinic acid | .500 | 9.0 | 9.0 | 9.0 | 9.0 | 9.0 | 9.0 | 8.7 |
| | .250 | 9.0 | 9.0 | 9.0 | 9.0 | 9.0 | 9.0 | 8.8 |
| | .125 | 8.6 | 9.0 | 9.0 | 9.0 | 9.0 | 9.0 | 9.0 |
| 2-(5-Isopropyl- | 8.000 | 9.0 | 9.0 | 9.0 | 9.0 | 9.0 | 9.0 | 8.0 |
| 5-methyl-4-oxo- | 4.000 | 9.0 | 9.0 | 9.0 | 9.0 | 9.0 | 9.0 | 9.0 |
| 2-imidazolin-2- | 1.000 | 9.0 | 9.0 | 9.0 | 9.0 | 9.0 | 9.0 | 9.0 |
| yl)-3-quinoline- | .500 | 8.8 | 9.0 | 9.0 | 8.9 | 9.0 | 9.0 | 8.5 |
| carboxylic acid | .250 | 8.3 | 8.8 | 9.0 | 8.6 | 9.0 | 9.0 | 8.0 |
| racemic mixture | .125 | 7.3 | 7.7 | 8.8 | 8.4 | 9.0 | 8.7 | 7.4 |

| Compound | RATE | RAG-WEED | VELVET-LEAF | S BARLEY LA | CORN FIELD | COTTON | RICE, NATO | SOY-BEAN AD |
|---|---|---|---|---|---|---|---|---|
| (+)-2-(5-Isopropyl- | .500 | 9.0 | 9.0 | 9.0 | 9.0 | 9.0 | 9.0 | 9.0 |
| 5-methyl-4-oxo-2- | .250 | 9.0 | 9.0 | 9.0 | 9.0 | 9.0 | 9.0 | 9.0 |
| imidazolin-2-yl)- | .125 | 9.0 | 9.0 | 9.0 | 9.0 | 9.0 | 9.0 | 9.0 |
| nicotinic acid | .063 | 8.0 | 9.0 | 9.0 | 9.0 | 9.0 | 9.0 | 9.0 |
| | .032 | 3.0 | 9.0 | 9.0 | 9.0 | 9.0 | 9.0 | 9.0 |
| | .016 | 1.0 | 9.0 | 9.0 | 9.0 | 8.0 | 9.0 | 8.0 |
| (−)-2-(5-Iso- | .500 | 9.0 | 9.0 | 9.0 | 9.0 | 9.0 | 9.0 | 9.0 |
| propyl-5-methyl- | .250 | 7.0 | 9.0 | 9.0 | 9.0 | 9.0 | 9.0 | 7.0 |
| 4-oxo-2-imida- | .125 | 7.0 | 9.0 | 9.0 | 9.0 | 9.0 | 9.0 | 5.0 |
| zolin-2-yl) | .063 | 1.0 | 9.0 | 9.0 | 7.0 | 8.0 | 9.0 | 4.0 |
| nicotinic acid | .032 | 0.0 | 9.0 | 9.0 | 5.0 | 7.0 | 9.0 | 3.0 |
| 2-(5-Isopropyl- | 10.000 | 8.0 | 8.0 | | | | | |
| 5-methyl-4-oxo- | 2.000 | 9.0 | 9.0 | | 9.0 | 9.0 | 8.0 | |
| 2-imidazolin-2- | 1.000 | 9.0 | 9.0 | 9.0 | 9.0 | 9.0 | 8.5 | 9.0 |
| yl)nicotinic acid | .500 | 8.8 | 8.8 | 9.0 | 9.0 | 9.0 | 8.7 | 9.0 |
| | .250 | 8.8 | 8.8 | 9.0 | 9.0 | 9.0 | 8.7 | 9.9 |
| | .125 | 8.6 | 8.8 | 9.0 | 9.0 | 9.0 | 8.7 | 9.0 |
| 2-(5-Isopropyl- | 8.000 | 9.0 | 8.0 | | | | 9.0 | |
| 5-methyl-4-oxo- | 4.000 | 9.0 | 9.0 | | 9.0 | | 9.0 | |
| 2-imidazolin-2- | 1.000 | 9.0 | 8.8 | 9.0 | 9.0 | | 9.0 | 6.5 |
| yl)-3-quinoline- | .500 | 8.9 | 8.5 | 9.0 | 9.0 | | 9.0 | 4.0 |
| carboxylic acid | .250 | 7.9 | 8.0 | 9.0 | 8.8 | | 9.0 | 3.6 |
| racemic mixture | .125 | 7.9 | 6.8 | 9.0 | 8.8 | | 8.8 | 2.6 |

We claim:

1. A process for the concomitant resolution-racemization-resolution of racemic amino nitriles of formula

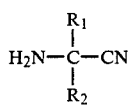

wherein $R_1$ is $C_1$–$C_4$ alkyl; $R_2$ is $C_1$–$C_4$ alkyl or $C_3$–$C_6$ cycloalkyl provided that when $R_1$ and $R_2$ are selected from $C_1$–$C_4$ alkyl, they cannot be the same, comprising: react molar amount of the above racemic aminonitrile with from 0.5 to 1.2 molar amount of resolved (+) or (−)-tartaric acid in the presence of a solvent of methanol, ethanol 2-propanyl or a mixture of methanol and methylene chloride, at a temperature range of from +5° C. to +50° C., for a period of time from one hour to forty hours or until essentially most of the racemic aminonitrile is converted to the optically active tartrate salt of the desired isomer.

2. A process according to claim 1, wherein $R_1$ and $R_2$ are both $C_1$–$C_4$ alkyl and are not the same, the solvent is methanol or a methanol-methylene chloride mixture, the amount of optically active tartaric acid is 0.75 to 1.0 mole per mole of racemic amino nitrile, the reaction temperature is from 15° C. to 40° C. and the reaction time is from 4 to 24 hours.

3. A process according to claim 1, wherein the amino nitrile is 2-amino-2,3-dimethylbutyronitrile; the solvent is methanol; the acid is (−)-tartaric acid in amounts of 0.75 to 1.0 mole per mole of racemic amino nitrile; the reaction temperature is from 15° C. to 40° C. the reaction time is from 4 to 24 hours.

4. A process according to claim 3, wherein the acid is (+)-tartaric acid.

* * * * *